United States Patent [19]
Strain et al.

[11] 3,948,281
[45] *Apr. 6, 1976

[54] GAS BLENDING USING NULL BALANCE ANALYZER

[75] Inventors: Donny R. Strain, Waterford; Daniel B. Martin, Troy, both of Mich.

[73] Assignee: Scott Environmental Technology, Inc., Plumsteadville, Pa.

[ * ] Notice: The portion of the term of this patent subsequent to Dec. 24, 1991, has been disclaimed.

[22] Filed: Oct. 26, 1973

[21] Appl. No.: 409,795

Related U.S. Application Data

[63] Continuation-in-part of Ser. No. 334,842, Feb. 22, 1973, Pat. No. 3,856,033.

[52] U.S. Cl. .................. 137/3; 137/93; 250/345
[51] Int. Cl.² .................................. G05D 11/08
[58] Field of Search .............. 137/3, 4, 5, 6, 88, 90, 137/91, 92, 93, 565; 141/20; 222/3; 73/23.1; 250/345, 346

[56] References Cited
UNITED STATES PATENTS

| | | | |
|---|---|---|---|
| 1,912,044 | 5/1933 | Schmidt | 137/6 |
| 2,813,010 | 11/1957 | Hutchins | 250/345 X |
| 2,927,501 | 3/1960 | Busignies et al. | 250/345 X |
| 3,451,402 | 6/1969 | Howard | 137/88 X |

*Primary Examiner*—Robert G. Nilson
*Attorney, Agent, or Firm*—Synnestvedt & Lechner

[57] ABSTRACT

The disclosure is directed to automatic flow blending of gas mixtures useful for calibrating gas analyzing instruments of the kind used in measuring atmospheric pollutants and the like. According to the disclosure the component gases reduced in pressure from the storage pressure, are continually mixed in a mixing zone at low pressure and pumped to high pressure for charging high pressure storage vessels. The mixture in the high pressure charging line is continuously monitored with a gas analyzer instrument. Variations from the desired blend are converted into an analog signal which is used to control various valve mechanisms for regulating the flow of gases to the low pressure mixing zone so that a match of the desired blend of gases is obtained.

10 Claims, 2 Drawing Figures

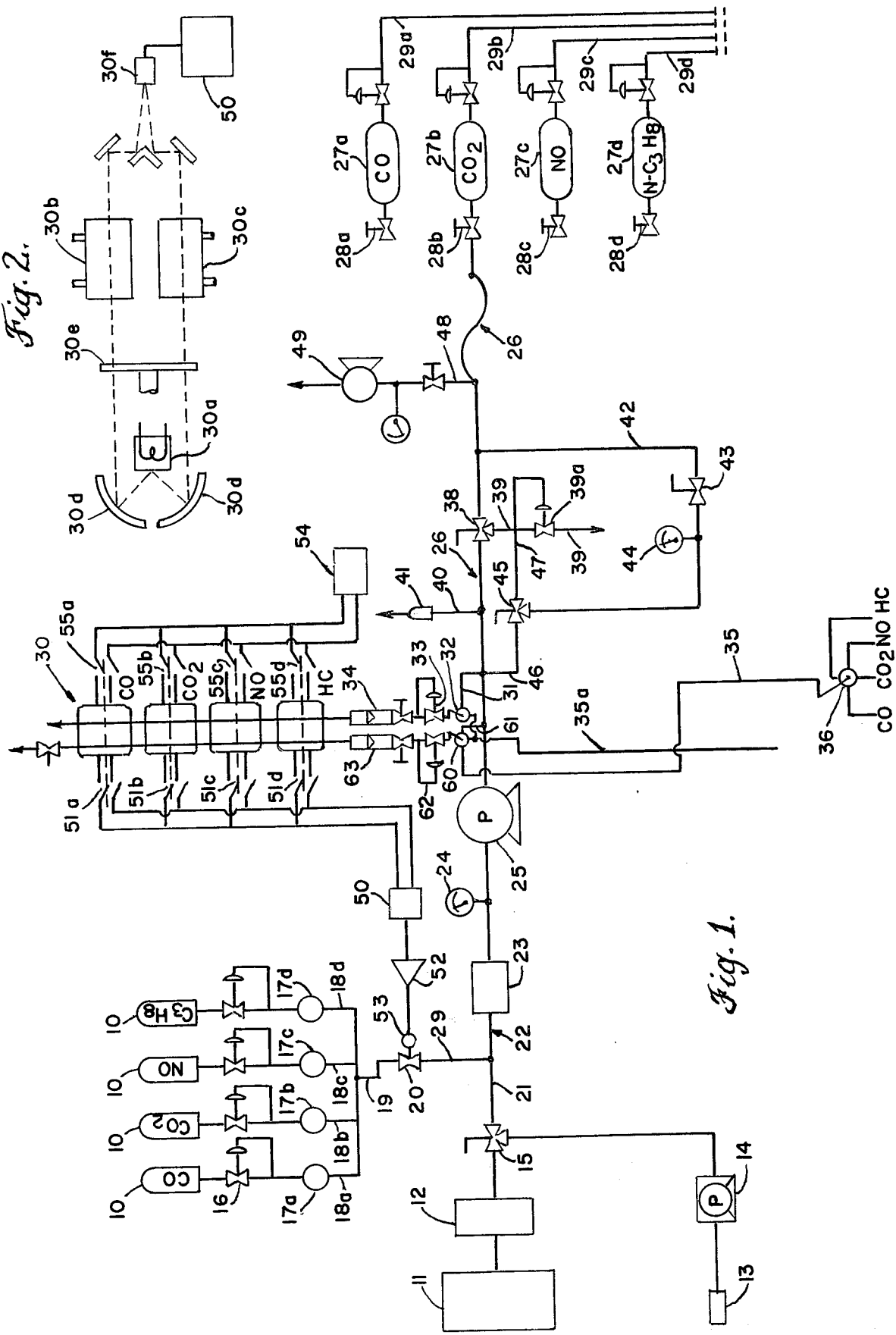

GAS BLENDING USING NULL BALANCE ANALYZER

RELATED APPLICATIONS

This application is a continuation-in-part of our copending application Ser. No. 334,842 filed Feb. 22, 1973 now U.S. Pat. No. 3,856,033, issued Dec. 24, 1974.

BACKGROUND OF THE INVENTION

1. Field Of The Invention

This invention relates to the blending of gases, and especially to the blending of calibration gases useful for the calibration of gas analysis instruments and the like. The present application contemplates certain alternative arrangements and further improvements as compared with the prior application above identified.

2. The Problem And The Prior Art

Calibration gases have been widely used in recent years for the calibration of instruments used in the analysis of mixtures of gases. The demand for calibration gases has become particularly active as a result of the need to accurately measure vehicle emissions as well as industrial stack emissions, chemical process streams, atmospheric pollutants, furnace atmospheres, life support atmospheres and the like. The need has been further stimulated by state and federal controls governing the emissions of carbon monoxide, hydrocarbons and other exhaust gas components and by various inspection and testing procedures which have evolved in order to make certain that motor vehicles meet the required emissions standards. Indeed, it is anticipated that in the very near future all automobiles manufactured will have to be tested as they leave the assembly line to make certain that the emission of the above pollutants is maintained within prescribed limits. It is also expected that automobiles now in use will be inspected periodically to determine whether or not they are being maintained in a proper state of tune so that they meet the same or similar high standards.

Present day techniques for gas analysis require the use of an instrument in which a so-called calibration gas having a composition which is precisely known is measured to produce an instrument response. One example of the manner in which this is accomplished involves the use of non-dispersive infrared analyzers. In these analyzers, the calibration gas is delivered to a cell through which a beam of infrared light is passed. The response of the instrument to the presence of the calibration gas, as indicated by the absorption of infrared energy, is observed and recorded. Thereafter the unknown gas is passed through the cell and similar observations taken. The concentration of the unknown gas may then be determined by observation of the instrument response and comparison with that obtained with the calibration gas.

With increasing need for these and similar instruments, the use of calibration gas has increased sharply in recent years. Typically, the calibration gas is supplied to the user in 43.6 liter cylinders which are pressurized to about 1500-2000 p.s.i. In preparing the gas mixtures, mixing is accomplished by the introduction of the components of the gas blend into the cylinder and pressurizing with the background gas such as nitrogen to the high pressure. The components of the blend behave differently at high pressures than they do under atmospheric conditions, not mixing well and exhibiting a tendency to stratify. This is apparently because the mean free paths of the various molecules are sufficiently shortened at the higher pressures so that the individual components do not diffuse readily. Mixing under high pressure is a time consuming and expensive process, involving prolonged heating and agitating of the cylinder in order to produce a commercially acceptable product. By way of example, mixing times by the prior art approach may be two hours or more in a typical case.

One drawback with the prior art batch approach described above arises because of the difficulties involved in precisely matching the mixture in one cylinder with that mixed at a previous time within the tolerances needed by industry. Since the measurement of exhaust emission often involves the use of computerized equipment associated with the analyzer, adjustments in the instrument and or in computer programs associated with and controlled by the instrument have to be made each time a new gas cylinder is used. This involves extra time and expense on the part of the user and is a potential source of error in the process of gas analysis.

Although laboratory techniques for blending gases at atmospheric pressures have been known in the art, so far as we are aware the use of these has been limited and there has been no recognition of the desirability of the production of gas blends in pressurized vessels, controlling the mixing at low pressures by a monitoring of the same blend of gases after they have been elevated in pressure.

Another prior art approach known to applicant involves the weighing in of components using a beam type scale on which the mixing vessel is weighed. Although accurate mixing of gas blends can be accomplished using this method, suitable beam type scales are extremely costly and great care must be taken to insure that external factors such as dirt, vibrations or the like do not result in errors in the weighing process.

A discussion of prior art methods for producing calibration gases may be found in NON-DISPERSIVE INFRA-RED GAS ANALYSIS, D. W. Hill and T. Powell, Plenum Press, New York, New York, 1968.

OBJECTS AND SUMMARY OF THE INVENTION

Having in mind the foregoing, an important object of the invention is the provision of equipment and method for generating gas mixtures of specified component concentrations within extremely close tolerances.

A related object of the invention is the provision of equipment and method for accurately comparing a blend being prepared with reference standards and modifying the blending operation to produce working standard mixtures in large volumes.

Another object of the invention is the provision of improved means and method for the rapid and efficient mixing of gas blends.

Still another object of the invention is the provision of improved means and method for achieving more complete mixing of gases than has heretofore been commercially practicable.

Still another object of the invention is the provision of large volume mixing techniques which make possible more economical production of gas blends on a mass production basis.

Still another object of the invention is the provision of an improved means for substantially automatically and accurately blending gases to conform to samples supplied by a customer.

Still another object of the invention is the provision of apparatus which makes possible the mixing of gases for calibration gas purposes within customer's storage vessels which are located at the point of end use. According to this aspect of the invention, the invention permits the continuous withdrawal of gas from the storage vessels by the customer during the refilling process thereby insuring the customer of an uninterrupted supply of gas.

A further object of the invention is the provision of means and method for gas blending which results in economies for both the blender and the user.

As in the prior application identified above, the present invention involves a recognition of the fact that gases depart from ideal behavior as the pressure of the gas mixture is raised. Complete mixing becmes much more difficult, evidently because the length of the mean free path of the gas molecules varies inversely with pressure, as a result of which the molecules of the components do not intermingle as freely at high pressure as they do at low pressure. Thus, gases mixed at high pressure may be stratified in the cylinders in which they are delivered to the end user, and even though great care was taken to measure the amounts of the components of the blend in the first instance, the customer will not get the desired blend out of the vessel unless great care is taken during the mixing process to properly and thoroughly mix the components.

According to the invention, substantially instantaneous, complete mixing of a blend of gases in desired concentrations is achieved by reducing the blending pressure of the gases to a relatively low pressure, e.g. preferably up to about two atmospheres and generally not exceeding about 50 p.s.i.g.

A gas pump is provided to pressurize the blended gas to the charging pressure at which the blend is to be stored. Flow control means regulate the proportions of gases delivered to the point of blending. Control mechanism for the flow control means includes null balance means for sensing departures of the blend of gases downstream from the pump from a sample blend and for regulating the flow control means to establish a blend which substantially matches the sample.

In carrying out the invention the sensing means establishes the proportions of the components of the blend delivered to the blending chamber by sensing the composition of a sample previously prepared. The sample may be derived from the customer's storage vessel or may be a standard reference mixture obtained from the National Bureau of Standards, or from other suitable sources.

The sensing means comprises a null balance dual beam type analyzer instrument. The reference mixture is delivered to one cell of the dual beam instrument and the gas being blended to delivered to the other cell. When the gas mixture being blended matches the reference sample, the instrument is in balance since equal amounts of energy are absorbed in the two cells. Departures from the zero or balance position provide an output signal which can be used to drive a feedback system which adjusts the proportions of the gaseous components of the mixture to precisely match the reference sample. Various connections are provided so that samples of numerous calibration gases may be matched, for instance at a customer's plant. Preparation of the apparatus for the production of a different kind of gas can be made simply and easily by merely evacuating the apparatus and purging so as to insure that no contamination of the new gas blend to be produced takes place.

THE DRAWING

In the detailed description of the illustrative embodiment, reference will be made to the accompanying drawings in which:

FIG. 1 shows a diagramatic form of a gas blending system incorporting the principles of the invention; and FIG. 2 is a schematic representation of a dual beam infrared analyzer instrument suitable for the purposes of the invention.

DETAILED DESCRIPTION OF THE INVENTION

With reference now to the drawings, wherein an illustrative embodiment of the invention is shown, the explanation which follows will be directed to the blending to two component mixtures of gas. Turning first to FIG. 1, the system described includes a source of supply for the components of a gas blend comprising a plurality of pressurized storage vessels 10 which are filled with supplies of a variety of gases such as carbon monoxide, carbon dioxide, nitric oxide and various hydrocarbons, four such supply vessels being shown in the drawing. Typically the gaseous mixtures comprise one of the gases identified above which is then mixed with a gas such as nitrogen or hydrocarbon-free air to obtain the desired ratio. Although the invention is described with reference to binary mixtures of gases, the extension of the invention to the blending of ternary and other multi-component mixtures will be obvious to those of ordinary skill in the art.

In the illustrative embodiment, the inert background gas such as nitrogen is supplied via a liquid or gaseous nitrogen supply vessel shown schematically at 11. A vaporizer 12 is used for the delivery of the nitrogen in gaseous form when supply vessel 11 contains liquid nitrogen. The gas supply means also includes means for alternatively supplying air from the atmosphere and includes atmospheric probe 13 and an air purifier and pump 14. Preferably, the pump should be hydrocarbon-free. In the illustrative embodiment of the invention, a pump having a rated capacity of 5000 cubic feet per hour at about 50 p.s.i.g. outlet pressure is provided.

A selector valve 15 is provided for selectively delivering air or nitrogen to a mixing chamber to be described subsequently.

Each of the gas supply vessels is provided with a pressure reducing valve 16 so as to reduce the pressure of the selected component to the desired mixing pressure, which is a pressure at which the gases to be blended thoroughly mix substantially instantaneously without agitation or heating. Although the mixing pressure may be as high as 100 p.s.i.g., preferred mixing pressures are within the range up to about 2 atmospheres and generally should not exceed about 50 p.s.i.g.

In order to select the component to be blended, the gas delivery means further includes selector valves 17a–d located in branch conduits 18a–d.

A conduit 19 leads from the junction of branch conduits 18a–d. Conduit 19 is provided with adjustable flow control means comprising a flow control valve or regulator 20 which regulates the flow of the components of the gas stream selected by operation of the selector valves 17a–d. Means for operating the flow control valve 20 will be described hereinafter.

Downstream of flow control valve or regulator 20, branch conduit 19 is connected to a conduit 21 leading from selector valve 15 and thus from the source of nitrogen or air. Downstream from the junction of conduits 19 and 21, a blending of the selected components takes place in a mixing passage 22 which may include a chamber 23 wherein the components are thoroughly intermixed at the relatively low pressures. A pressure gauge 24 is located in the relatively low pressure mixing zone and as shown in the drawing is between the mixing chamber 23 and a gas pump or compressor 25.

According to the illustrative embodiment of the invention, compressor 25 is a positive displacement multi-stage pump for compressing the blended gas (typically under pressures on the order of 2000 p.s.i.g.). The outlet of the compressor is connected to a conduit or charging line 26 which leads to a fitting to which a selected storage vessel may be connected. Four such vessels are shown by the reference characters 27a through 27d respectively, each being provided with a valve 28a through 28d. According to one preferred method of utilization of the invention, the storage vessels 27a through 27d are relatively large vessels, for example on the order of 50 cu. feet (internal volume). These vessels may be located at the customer's plant, in which case the gas is immediately available for use in the customer's instruments via suitable manifolding. As an alternative, large storage vessels may be located at the gas blending plant in which case the blended gas may be transferred to smaller cylinders suitable for transportation and delivery to customers. Whatever the case, each of these vessels has an outlet line identified as 29a through 29d respectively, each of which is provided with pressure limiters and with suitable control valving and with couplings (not shown).

It is important that the compressor 25 be oil-free and that all parts coming into contact with the gas stream should be inert with respect to the hydrocarbons or other constituents of the gases to be blended. Various positive displacement pumps now on the market are suitable for the purpose. In addition to the criteria discussed above, in selecting a unit it should be added that the low pressure mixing zone must be completely isolated from the high pressure zone so that back pressure effects do not influence the pressure at which mixing takes place.

The invention includes means for sensing and analyzing the gas blend on the high pressure side of the pump. Although various other analyzing means capable of comparing a gas blend with a reference or sample blend could be employed, in the preferred embodiment, a conventional non-dispersive, infrared analyzer of known construction is used, the analyzer being identified by the reference character 30. According to the preferred embodiment, analyzer 30 is comprised of a plurality of individual instruments, each sensitized to measure one of the gases that it is contemplated will be blended. A form of analyzer instrument suitable for the purposes of present invention is shown in FIG. 2. In the illustrative embodiment the instrument is provided with a single infrared source 30a. Infrared energy from source 30a is passed through cells 30b and 30c by means of mirrors 30d. A rotating chopper 30e causes a periodic change in the energy impinging on detector 30f. According to the invention, a sample or reference gas is delivered to cell 30b by piping to be described hereinafter. Cell 30c is connected to the downstream, high pressure side of the pump so that it receives the gas which is blended in the mixing zone 23 after the gas passes through the pump 25. The infrared radiation passing through the cells 30b and 30c, is absorbed by the molecules of the gases in the cells. When the absorption characteristics in each cell are identical, that is, when the gas being blended exactly matches the sample or reference gas, there is no output signal. However, when the gas being blended departs from the reference sample an output reading is obtained which drives servo-mechanism circuitry to change the proportions of the components of the gas blend until the gases in the two cells match. A high sensitivity to departures of the gas being blended from the reference mixture can be obtained by the system, since slight departures from a null balance or zero condition are more readily detected than is the case when such an instrument is used in the positive deflection mode and can be used for the purposes of driving the servo-mechanism. It should be understood that the invention is not to be limited to the use of infrared analyzers, since other analyzer instruments capable of measuring the concentrations of a reference gas and a gas being blended and being capable of operating on a null balance principle are known in the art and may be employed.

Cell 30c of each instrument comprising analyzer 30 is connected to the downstream, high pressure side of the compressor via a line 31, which leads to a valve 32. A pressure regulator 33 drops the pressure to a pressure which is about the same as the pressure at which the blend is being mixed. A flow meter with an integral valve, generally designated with reference character 34 is located downstream of the pressure regulator for regulating the flow to the desired value.

Selector valve 32 is typically a manually operable valve with the common port in communication with pressure regulator 33. One port of valve 32 is in communication with conduit 26 via a line 31.

A sample line 35 is connected to another inlet port of a selector valve 60 and provides for delivery of a known sample of reference gas such as an NBS standard reference mixture via line 35 from another selector valve 36 whose inlet ports are connected to the reference blends. In addition, a line 61 leads from the line 26 to selector valve 60 so that a sample from the customer's tank may be delivered to cell 30b. Downstream from selector valve 60 there is provided a pressure regulator 62 for maintaining the pressure in cell 30b at the same level as in 35a and a flow controller 63. A valve 64 is provided to hold the reference gas in the appropriate cell 30b if desired. A line 35a leads to another port of selector valves 32 and 60 for supply of nitrogen or air, used for flushing out and zeroing the instrument.

Also located in the charging line downstream from the junction with line 31 is a 180° three port valve 38. Valve 38 is movable from an off position in which flow through line 26 is blocked to a position in which flow through the line is permitted or to a venting position in which flow from the pump is vented to atmosphere via vent line 39. A pressure regulator 39a is located in the vent line and is adjustable so that during start-up, pump pressure can be limited to the pressure in the particular vessel 27a–d which is to be filled.

As indicated, in addition to the facility for furnishing the instrument with calibration or references gases via the line 35, a sample may be taken directly from a selected partly filled storage vessel 27a through 27d or from the customers partially used cylinder.

Also located in line 26 is another vent line 40 which is equipped with a pressure relief valve 41. This valve is set to open at a suitable predetermined upper limiting pressure such as 2500 p.s.i.g.

A line 42 is connected to line 26 downstream from valve 38. Line 42 is provided with a manually operable 90° ball valve 43, a pressure gauge 44 and a 180° selector valve 45 for selectively directing the gas to a line 46 or to the vent line via a line 47. The vent line 39 as indicated above, is provided with an adjustable back pressure regulator valve 39a. Line 46 leads to the charging line 26 on the upstream side of valve 38 and provides a flow path back to the analyzer instrument when valve 38 is closed.

A line 48 interconnects line 26 with a vacuum pump 49 for use when it is desired to purge the system of a particular gas which was previously blended.

As indicated above, the means for analyzing the gas, identified by the reference character 30 in the drawing, in a typical installation comprises several non-dispersive infrared analyzer instruments, each of which is provided with a sample cell 30c for measuring and comparing the concentration of one of the components of a gas to be blended with a reference gas in a second or reference cell 30b. Four such analyzer instruments of identical construction are shown in the illustrative embodiment, each of which is set up to measure the concentration in the blend of one of the four gas components in the supply vessels 10. Other types of instruments, as for example non-dispersive ultraviolet, flame ionization, flame emission or thermal conductivity analyzers may be employed.

The individual analyzers are selectively connected to control mechanism 50, by suitable switch means schematically shown in the drawing and indicated by the reference characters 51a through 51d respectively. Control mechanism 50 forms a part of a servo mechanism also including the positioner 52 and a balancing motor 53 which adjusts the relative concentrations of the components being blended in accordance with departures from the reference blend as sensed by the analyzer, so that a precise match with the preselected blend is maintained.

A suitable strip chart recorder 54 connectible to the analyzers by means of switches 55a through 55d may also be provided.

In use, two modes of operating practice are followed. When a blend already in a storage vessel to be charged, such as one of the vessels 27a–27d, is to be matched, preferred operating practice is to connect the selected storage vessel to the charging line 26 with all system valves closed. The valve 28a–d for the selected storage vessel is opened as is 90° valve 43 and the vessel pressure is then read on gauge 44. 180°Valve 45 is turned to the position in which some of the original gas in the storage vessel is vented out through line 47 and vent line 39 so that the lines are purged. 180° Valve 45 is then turned to the opposite position so that gas from the vessel flows through line 26, line 42, line 46, line 61, selector valve 60, pressure limiter 62 and flow regulator 63. The gas flows through the analyzer. Valve 64 is closed as is selector 60 and the response of the instrument is noted. Valve 43 is then closed.

The 180° valve 38 is next turned to the position in which compressor output is vented through back pressure regulator 39a. The compressor is then started and the back pressure regulator is adjusted to obtain the same pressure as that of the storage vessel. The 180° valve 38 is next rotated to the position in which the mixture is pumped into the storage vessel, the vessel valve 28b being also open. As the vessel is filled, the output of the compressor is continuously monitored on the analyzer 30 via selector valve 32. The absorption characteristics of the gases in cells 30b and 30c are compared and the controller 50 adjusts the valve 20 to always maintain the mixture at the precise concentration originally in the vessel.

According to the other mode of operating practice, a calibrated sample is delivered to cell 30b via selector valve 36, sample line 35 and selector valve 60. The controller is adjusted to deliver gases in approximate concentration. Selector valve 32 is set in the position in which line 26 is in communication with the analyzer so that the gas delivered by the compressor is continuously monitored. With the pump operating, the gas being blended flows through the cell 30c. As stated above, differences in the absorption characteristics of the reference sample blend and the blend being prepared produce an output signal to control mechanism 50 which is used to adjust valve 20 so that the blend exactly matches the reference gas.

Since mixing takes place at a pressure at which there is no tendency of the components to stratify, the blend is mixed more thoroughly and substantially instantaneously. The entire mixing apparatus is quite compact and the customer is assured of getting a concentration of gases which nearly exactly matches a reference sample or the concentration he previously used. Time consuming agitation and heating is unnecessary. Inasmuch as the blend in the high pressure vessels is being continuously measured, it provides the control parameter for low pressure blending.

The invention described provides equipment which is simple to operate and maintain and in accordacne with one important aspect of it, the entire system may be truck or trailer mounted so that it can be driven to the customer's facility where the customer's gas storage vessels are located. The blending apparatus is connected to the storage vessel, the blend in the vessel analyzed, matched and continuously monitored during the refilling process. In this manner the customer is assured of a continual supply of a gas blend of unvarying concentration and may even continue to draw off gas for use during the blending operation.

We claim:

1. Equipment for flow blending of gases useful for instrument calibration and the like comprising gas supply means for supplying the components of a gas blend including adjustable flow regulating means for selectively regulating the flow of at least one of said components relative to an other, a gas blending passage downstream of the flow regulating means for low pressure blending of the components, means for limiting the blending pressure to a pressure at which the gas components of the blend mix substantially instantaneously, a gas compressor having a low pressure inlet connected to said gas blending passage and an outlet, a gas blend analyzer means comprising a first analyzing device for analyzing a sample of a gas to be matched, a second analyzing device in communication with the compressor outlet for measuring the proportions of the gas mixture being blended and control means operable by said analyzer means and being responsive to departures of the gas mixture being blended from the sample for operating said flow regulating means to regulate the proportions of said components to match the gas mixture actually being blended with the sample.

2. Equipment according to claim 1 further including means for selectively interconnecting the charging line and the first analyzing device whereby a sample of a gas in a storage vessel can be delivered to said first analyzer device for use as a reference sample.

3. Equipment for charging high pressure storage vessels with a mixture of gases substantially identical to the mixture remaining in the vessel comprising gas supply means for the supply of the gaseous components of the mixture, said supply means including a flow control valve means for regulating the flow of at least one of the components relative to another, a mixing conduit for the gases, means for limiting the mixing pressure to a pressure at which mixing of the components takes place substantially instantaneously, a high pressure gas compressor having an inlet connected to the mixing conduit and a high pressure outlet, a charging line connected to the high pressure outlet for charging a storage vessel gas mixture analyzer means including a first null balance analyzing device for analyzing the mixture of the gases downstream from the compressor, a second null balance analyzing device for analyzing a reference sample, and means controlled by said first and second analyzer devices and responsive to departures of the mixture being blended from the preselected sample for regulating said flow control valve means for matching said mixture with the preselected sample.

4. Equipment for flow blending of gases useful for instrument calibration and the like comprising gas supply means for supplying the components of a gas blend including adjustable flow regulating means for selectively regulating the flow of at least one of said components relative to an other, a gas blending passage downstream of the flow regulating means for low pressure blending of the components, means for limiting the blending pressure to a pressure at which the gas components of the blend mix substantially instantaneously, a gas compressor having a low pressure inlet connected to said gas blending passage and an outlet, a gas blend analyzer means comprising a first analyzing device for analyzing a sample of a gas to be matched, a second analyzing device in communication with the compressor outlet for measuring the proportions of the gas mixture being blended and control means operable by said analyzer means and being responsive to departures of the gas mixture being blended from the sample for operating said flow regulating means to regulate the proportions of said components to match the gas mixture actually being blended with the sample.

5. A method of charging a partly filled pressurized storage vessel with a thoroughly mixed blend of gases, the concentrations of which match the concentrations of the blend which is already in the vessel, wherein the charging pressure is a pressure at which the gaseous components of the blend do not freely intermix, which method comprises passing the blend in the pressurized vessel to a first analyzer device and measuring the concentration of the components of the blend in the pressurized vessel with said analyzer device, feeding the components of the blend from separate sources to low pressure mixing zone, mixing the components of the blend in the mixing zone at a pressure at which the components of the blend freely intermix, compressing the mixture and filling the vessel with the compressed mixture, measuring the concentration of the components of the compressed mixture with a second analyzer device and adjusting the feed to the low pressure mixing zone in a sense to compensate for departures of the concentrations of the mixture as measured by said second analyzer device from the mixture previously in the vessel as measured by said first analyzer device to thereby match the mixture previously in the vessel.

6. Equipment for charging a high pressure storage vessel with a mixture of gases, the components of which mixture are present in substantially identical quantities to the mixture remaining in the vessel, comprising gas delivery means for the supply of gaseous components of the mixture, said supply means including a flow regulating valve for regulating the flow of at least one of the components relative to another, a mixing conduit for the gases, means for limiting the mixing pressure to a pressure at which mixing of the components takes place substantially instantaneously, a high pressure gas compressor having an inlet connected to the mixing conduit and a high pressure outlet, a charging line connected to the high pressure outlet for charging a storage vessel needing replenishment at a relatively high pressure, gas mixture analyzer means for analyzing the concentration of the components of the mixture of the gases downstream from the compressor, said analyzer means comprising a plurality of analyzer devices in communication with the charging line, selector valve means operable in one position for connecting one of a plurality of samples of gases to one of said analyzer devices and in another position for connecting said charging line to another of said analyzer devices, and means responsive to departures of the concentrations of the components of the mixture from a preselected sample for regulating said flow control valve for matching the mixture with the preselected sample.

7. Equipment for charging a high pressure storage vessel with a thoroughly mixed blend of gases having a desired predetermined percentage composition based on the percentage composition of a sample derived from said storage vessel or from some other previously calibrated mixture, wherein the charging pressure is a pressure at which the gaseous components of the blend do not freely intermix, comprising gas delivery means for the supply of the gaseous components of the blend including flow regulating valve means for regulating the flow of at least one of the components relative to another, a mixing conduit for mixing the blend of gases, means for limiting the pressure in the mixing conduit to a level at which mixture of the components of the blend takes place substantially instantaneously, a high pressure gas compressor having an inlet connected to the mixing conduit for pressurizing the mixed gases to said charging pressure, a charging line connected to the outlet of said compressor for delivering the pressurized gas to a storage vessel needing replenishment, gas blend analyzer means comprising a first gas analyzing device and a second gas analyzing device, valve means providing for connection of one of said analyzer devices alternatively with the storage vessel or said previously calibrated reference mixture whereby a reference sample derived from either source may be analyzed, said last named valve means further providing for connection of the second analyzer device with said charging line, whereby the percentage composition of the pressurized mixture delivered by said compressor may be continuously monitored, and means providing for adjustment of the flow regulating valve means in a sense which effects matching of the percentage composition of the compressed mixture as measured by the second analyzer device with the desired predetermined percentage composition as measured by the first analyzer device.

8. A method of charging a high pressure storage vessel with a thoroughly mixed blend of gases having a desired predetermined composition, the components of which are in known concentration, wherein the charging pressure is a pressure at which the gaseous components of the blend do not freely intermix, which method comprises deriving a reference sample alternatively from the storage vessel or from a previously calibrated mixture, measuring the percentage composition of the reference sample on a first analyzer device, feeding the components of the blend from separate sources to a low pressure mixing zone wherein the pressure is maintained at a level at which the components of the blend freely intermix, compressing the low pressure mixture to the charging pressure, measuring the percentage composition of the compressed mixture on a second analyzer device and adjusting the feed to the low pressure mixing zone in accordance with variations of the actual percentage composition of the compressed charging mixture in relation to the percentage composition of the measured sample composition in a sense which effects matching the composition of the compressed mixture with the desired predetermined composition.

9. A method of charging a high pressure storage vessel with a thoroughly mixed blend of gases having a predetermined composition, wherein the components of the blend are present in desired concentrations and wherein the charging pressure is a pressure at which the gaseous components of the blend do not freely intermix, which method comprises deriving a reference sample having the predetermined composition alternatively from the storage vessel or from a previously calibrated mixture, measuring the concentrations of the components of the reference sample with a first analyzer device, feeding the components of the blend from separate sources to a low pressure mixing zone wherein the pressure is maintained at a level at which the components of the blend freely intermix, compressing the low pressure blend to the charging pressure, measuring the concentrations of the components of the compressed blend with a second analyzer device and adjusting the feed to the low pressure mixing zone in accordance with departures of the actual concentration of the components of the compressed charging blend from the measured concentration of the components of the sample in a sense which effects matching of the composition of the compressed blend with the predetermined composition.

10. A method according to claim 9 wherein the mixing zone is maintained at a pressure below 50 p.s.i.g.

* * * * *

UNITED STATES PATENT AND TRADEMARK OFFICE
CERTIFICATE OF CORRECTION

PATENT NO. : 3,948,281
DATED : April 6, 1976
INVENTOR(S) : Donny R. Strain & Daniel B. Martin It is certified that error appears in the above-identified patent and that said Letters Patent are hereby corrected as shown below:

Column 3, line 17, "becmes" should be --becomes--.

Column 3, line 56, "to" second occurrence should be -- is --.

Column 4, line 10, "incorporting" should be --incorporating--.

Column 4, line 19, "to" first occurrence should be -- of --.

Claim 4 should be --Apparatus according to claim 3 further including selector valve means operable to selectively connect one of a plurality of samples of gases or said charging line to said second analyzer means.--

Signed and Sealed this twenty-second Day of June 1976

[SEAL]

Attest:

RUTH C. MASON
Attesting Officer

C. MARSHALL DANN
Commissioner of Patents and Trademarks